(12) United States Patent
Moghe et al.

(10) Patent No.: US 9,238,140 B2
(45) Date of Patent: Jan. 19, 2016

(54) CURRENT LEAKAGE DETECTION

(75) Inventors: Yashodhan Moghe, Lane Cove (AU);
Helmut Christian Eder, Castle Hill (DE)

(73) Assignee: Cochlear Limited, Macquarie University, NSW (AU)

( * ) Notice: Subject to any disclaimer, the term of this patent is extended or adjusted under 35 U.S.C. 154(b) by 1179 days.

(21) Appl. No.: 12/438,942

(22) PCT Filed: Aug. 24, 2007

(86) PCT No.: PCT/AU2007/001224
§ 371 (c)(1),
(2), (4) Date: Mar. 29, 2010

(87) PCT Pub. No.: WO2008/022404
PCT Pub. Date: Feb. 28, 2008

(65) Prior Publication Data
US 2012/0191160 A1    Jul. 26, 2012

(30) Foreign Application Priority Data
Aug. 25, 2006  (AU) .................. 2006904624

(51) Int. Cl.
*A61N 1/37*        (2006.01)
*A61N 1/05*        (2006.01)
*A61N 1/36*        (2006.01)
*G01R 19/00*       (2006.01)
*G01R 31/02*       (2006.01)

(52) U.S. Cl.
CPC .......... *A61N 1/3706* (2013.01); *G01R 19/0092* (2013.01); *G01R 31/025* (2013.01)

(58) Field of Classification Search
CPC ..... A61N 1/0541; A61N 1/08; A61N 1/3605; A61N 2001/083
USPC .......................... 607/2, 57, 137, 27; 323/315
See application file for complete search history.

(56) References Cited

U.S. PATENT DOCUMENTS

| 4,584,635 | A | * | 4/1986 | MacInnis et al. | 363/25 |
| 5,481,194 | A | * | 1/1996 | Schantz et al. | 324/522 |
| 5,999,849 | A | * | 12/1999 | Gord et al. | 607/2 |
| 6,011,398 | A | * | 1/2000 | Bald et al. | 324/511 |

(Continued)

FOREIGN PATENT DOCUMENTS

| EP | 0479099 B2 | 1/2000 |
| JP | 2003315374 | 11/2003 |

(Continued)

OTHER PUBLICATIONS

International Search Report. PCT/AU2007/001224. Mailed Sep. 18, 2007.

(Continued)

*Primary Examiner* — Christopher A Flory

(57) ABSTRACT

An improved arrangement for detecting DC current leakage in implanted devices is disclosed. Currents are monitored, so that any unexpected imbalance indicates that a fault condition has occurred. The principle of the system is that if everything working correctly, the same current should be flowing into the tissue from VDDH-ELEC as is passing out of the tissue into VSS_ELEC. Any difference is indicative of current flowing into or out of the tissue from unknown paths, which is indicative of some fault. This replaces routine monitoring for specific faults.

20 Claims, 2 Drawing Sheets

(56) References Cited

U.S. PATENT DOCUMENTS

| | | |
|---|---|---|
| 6,096,062 A | 8/2000 | Silvian |
| 6,144,881 A * | 11/2000 | Hemming et al. ............... 607/28 |
| 6,358,281 B1 | 3/2002 | Berrang et al. |
| 6,542,777 B1 | 4/2003 | Griffith et al. |
| 7,962,222 B2 * | 6/2011 | He et al. ........................... 607/61 |
| 2005/0024245 A1 * | 2/2005 | Sit et al. ......................... 341/119 |
| 2005/0225909 A1 | 10/2005 | Yoshizaki et al. |
| 2005/0237680 A1 | 10/2005 | Egner |
| 2006/0187594 A1 | 8/2006 | DiSalvo |
| 2006/0247684 A1 | 11/2006 | Halperin et al. |
| 2007/0265686 A1 | 11/2007 | Greenberg et al. |
| 2008/0071168 A1 | 3/2008 | Gauglitz et al. |
| 2008/0154342 A1 | 6/2008 | Digby et al. |
| 2010/0274319 A1 | 10/2010 | Meskens |
| 2011/0208269 A1 * | 8/2011 | He et al. .......................... 607/61 |

FOREIGN PATENT DOCUMENTS

| | | |
|---|---|---|
| WO | 9534824 | 12/1995 |
| WO | WO 97/01314 | 1/1997 |
| WO | WO 2006/124481 | 11/2006 |
| WO | WO 2008/022404 | 2/2008 |
| WO | WO 2009/127014 | 10/2009 |
| WO | WO 2010/000027 | 1/2010 |

OTHER PUBLICATIONS

Arabi et al., "Design and Realization of an Accurate Built-In Current Sensor for On-Line Power Dissipation Measurement and IDDQ Testing", International Test Conference, 1997 IEEE, Paper 24.2, pp. 578-586.

* cited by examiner

CURRENT LEAKAGE DETECTION

CROSS-REFERENCE TO RELATED APPLICATIONS

This application is a national stage application under 35 USC §371(c) of PCT Application No. PCT/AU2007/001224, entitled "CURRENT LEAKAGE DETECTION METHOD AND DEVICE," filed Aug. 24, 2007, which claims priority to Australian Patent Application No. 2006904624, filed Aug. 25, 2006, which is hereby incorporated by reference herein.

FIELD OF THE INVENTION

The present invention relates to a current leakage detection device and method for implanted devices.

BACKGROUND OF THE INVENTION

Implanted devices, such as heart pacers and cochlear implants, have been widely deployed to assist with the management of various indications. The present invention is particularly concerned with devices which are electrically powered.

Engineers and technicians have, with improvements in technology and knowledge, been making the devices smaller and therefore more readily implantable. Improvements to functions and the increased complexity of devices and functions are an important part of the progressive development of implantable devices. However, as implantable devices become increasingly complex, the potential for electrical failures increases.

Such failures can result in DC current leakage, with the excess DC current passing through tissue of the implantee in ways which are not related to therapy. Such DC currents flows could result in electrolysis, or otherwise cause injury to the user. DC currents can also cause irreversible redox reactions at the electrodes of the implanted device.

By way of example, current cochlear implants are capable of detecting fault conditions in only a very limited way, usually by regularly checking for particular faults. The faults being checked for are programmed into the implant based on the failure modes determined by the design team. For example, electrodes may short to ground. As devices become more complex, the number of failure modes that can lead to DC current leakage increases dramatically. As such, the present methods of checking for faults will take an increasing amount of time and power, and be increasingly complex to design and operate. Further, it becomes increasingly difficult to determine all possible failure modes, and to try to detect each specific failure mode.

It is accordingly an object of the present invention to provide a simplified method and apparatus for detecting current leakage in implantable devices.

SUMMARY OF THE INVENTION

In a broad form, the present invention provides a method of determining when a DC current leakage has occurred in an implanted device irrespective of the cause of the DC current leakage, wherein current flows are compared to detect an unexpected imbalance.

In one aspect, the present invention provides a method of detecting DC current leakage in an electrical circuit of an implanted device, said method including at least the steps of:

a) measuring, for each intended current path connected to one or more predetermined points in the circuit, the current flow relative to the direction of the point;

b) summing each measured current flow to provide a total current;

c) determining whether the total current is within a predetermined margin of zero;

wherein if the total current is not within said predetermined margin of zero, determining that leakage current is present.

In a second aspect, the present invention provides a method of detecting DC current leakage in an implanted device, said device including electrical output driving circuits powered by a respective power and ground rail, said method including at least the steps of:

a) measuring the current passing through the power rail;

b) measuring the current passing through the ground rail;

c) comparing the first and second measurements; and if there is a absolute difference greater than a predetermined margin between first and second measurements, determining that current leakage is present.

According to another aspect, the present invention provides an implantable device including electrical output driving circuits powered by a respective power and ground rail, a first current monitoring device for said power rail, a second current monitoring device for the ground rail, and a comparator for comparing the first and second current monitoring device, such that if the comparator detects a difference greater than a predetermined margin, an indication is provided that current leakage is occurring.

A determination that there is current leakage indicates that a fault of some sort appears to be present, and may lead to various actions, for example the activation of specific diagnostic software. It provides predominantly an overall indication that a fault is occurring, and existing diagnostic software can be used to identify and rectify or isolate the fault, or in an extreme situation, shut down the implant.

The predetermined margin is required to allow for small errors and variations in the respective devices, and may be determined by the device designer on the basis of the accuracy and tolerances of the device. A time aspect may also be included to account for transient events.

An advantage of the inventive approach is that it minimizes the need for identification in advance of all possible faults, and for monitoring software to continuously check for all these faults. Maintenance processes can be run at suitable times, with consequently less degradation of the performance of the implant due to the operation of checking and verification processes running in parallel with the intended function of the implant.

Whilst the present invention may be applied to any implanted device, it is particularly envisaged as applicable to implantable devices which are intended to deliver electrical signals, for example cochlear implants.

BRIEF DESCRIPTION OF THE DRAWINGS

An illustrative embodiment of the present invention will be described with reference to the accompanying figures, in which.

DESCRIPTION OF PREFERRED EMBODIMENT

Figure 1:
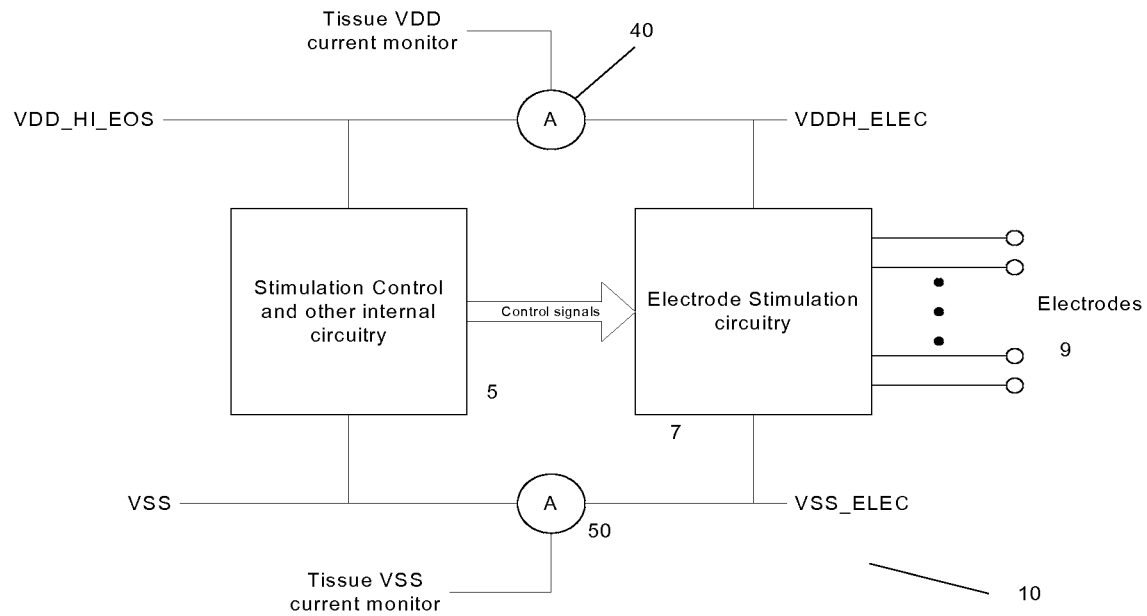
FIG. 1 shows a schematic overview of one embodiment of the invention in a broad form.
Figure 2:
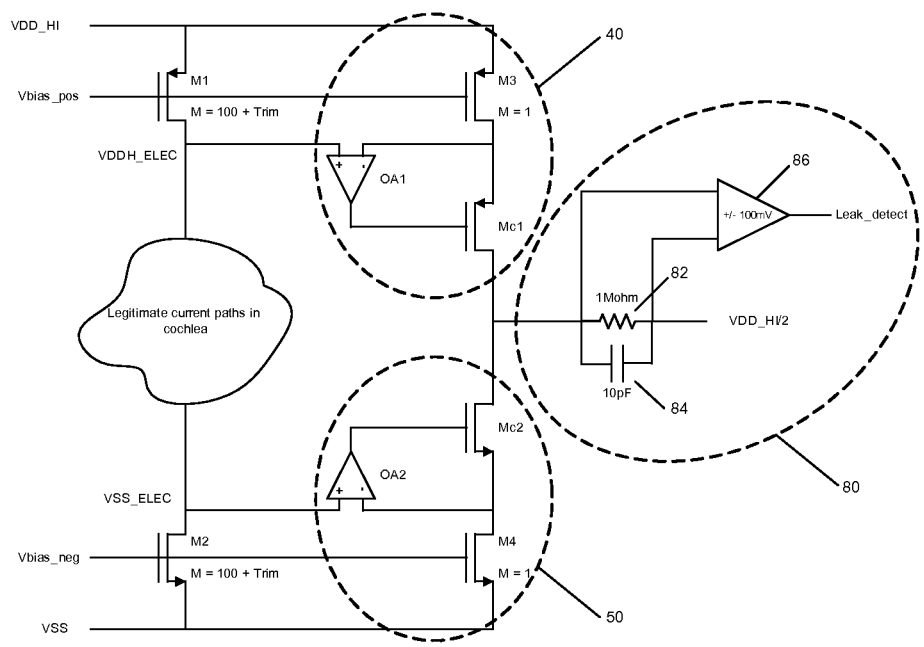
FIG. 2 shows a block diagram of an embodiment of the invention.

FIGS. 1 and 2 show an example of a system 10 used to monitor the current flowing in an implanted device. In the example shown, the implanted device is a cochlear implant, and the implementation of the leakage current detector is a low-power form suitable for integration into a cochlear implant.

It will be appreciated that the present invention can be applied to a wide variety of implantable devices, in which DC leakage current is a potential issue. The example used below is a cochlear implant, but the present invention is applicable to many other devices, for example other implanted hearing aids or hearing prostheses, neural stimulators, retinal prostheses, cardiac related devices such as pacers or defibrillators, implanted drug pumps, or other implanted electrical devices.

FIG. 1 is a schematic overview of this implementation of the invention, within an integrated circuit which provides the electrical circuitry for operation of the implanted device. Box 5 represents the stimulation control and other internal circuitry, which sends control signals to the electrode stimulation circuitry 7, which in turn delivers electrical stimuli to selected electrodes 9 in accordance with the control signals. This is a well known arrangement in cochlear implants, and as the present invention is not concerned with the details of stimuli presented or stimulation generation as such, this aspect will not be described in detail. Cochlear implants of this general type are disclosed, for example, in U.S. Pat. No. 4,532,930 to Crosby et al. The stimuli delivered by the electrodes 9 constitute the desired electrical output from the system: any DC current otherwise delivered by the implant is indicative of a fault.

The stimulation power rail VDD-HI is the power rail for the system as a whole, and VSS is the corresponding ground rail. According to this implementation of the present invention, an additional stimulation power rail VDDH_ELEC, and an additional stimulation ground VSS-ELEC, are provided internal to the integrated circuit. The additional rails provide the power for the electrode stimulation circuitry 7. The currents in VDDH_ELEC and VSS-ELEC are monitored by suitable measuring arrangements, shown here as A1 and A2 respectively.

The principle of the system is that if everything is working correctly, the same current should be flowing into the tissue from VDDH_ELEC as is passing out of the tissue into VSS-ELEC. This is the known current path. Any difference is indicative of current flowing into or out of the tissue from unknown paths, which is indicative of a fault of some kind.

This system takes advantage of Kirchoff's current law in which the sum of currents flowing towards a point in a circuit is equal to the sum of currents flowing away from that point. Due to Kirchoff's current law, the total sum of currents entering the tissue in an implanted device is zero. If the sum of current entering along known paths is not zero, then the left-over current must be entering the tissue along an unknown or fault path. Therefore, should a comparison of $A_1$ and $A_2$ find a difference between the current flow there is a DC current leakage and hence a fault of some kind.

FIG. 2 illustrates in more detail a practical implementation of this approach. Circuit 40 acts as a current mirror for the current through M1, which is effectively the current flowing into VDDH_ELEC. Similarly, circuit 50 acts as a mirror of the current in M2, which is effectively the current in VSS-ELEC. Circuit 80 is a comparator, which detects any current difference between M1 and M2.

A current mirror is a circuit which accurately tracks the current in another circuit, but in this case scaled down by a factor of 100. It is designed to copy a current flowing through an active device by controlling the current in another active device of a circuit, keeping the output current constant regardless of loading. The current being 'copied' can be, and sometimes is, a varying signal current. Any current mirror, such as bipolar or MOSFET, may be used; the one shown is a MOSFET current mirror. The comparator working on the output of the current mirrors in an optimally operating circuit according to the present embodiment will detect no difference in current. The mirror circuits used should be very sensitive to differences in current, and accurately match the currents in the monitored circuits. In this application, it is desirable to be able to detect a difference of about 10 μA between M1 and M2, on top of a common mode current of about 10 mA. This requires 0.1% accuracy in the ratio of M1/M3 to M2/M4, which is close to the limit of what is achievable with this arrangement.

The resolution can be increased by decreasing the mirroring ratio. However, this occurs at the expense of increased power consumption of the monitoring system.

The comparison of the currents mirrored at monitors 40, 50 is accomplished by comparator 80. The resistor 82 senses the current difference. The capacitor 84 suppresses or filters out temporary mirroring imbalances due to current switching spikes such as onset of stimulation pulses. The voltage across resistor 82 is compared at a bi-directional voltage comparator 86. The comparator is capable of detecting a 10 μA difference between VDDH_ELEC and VSS-ELEC.

Figure 3:
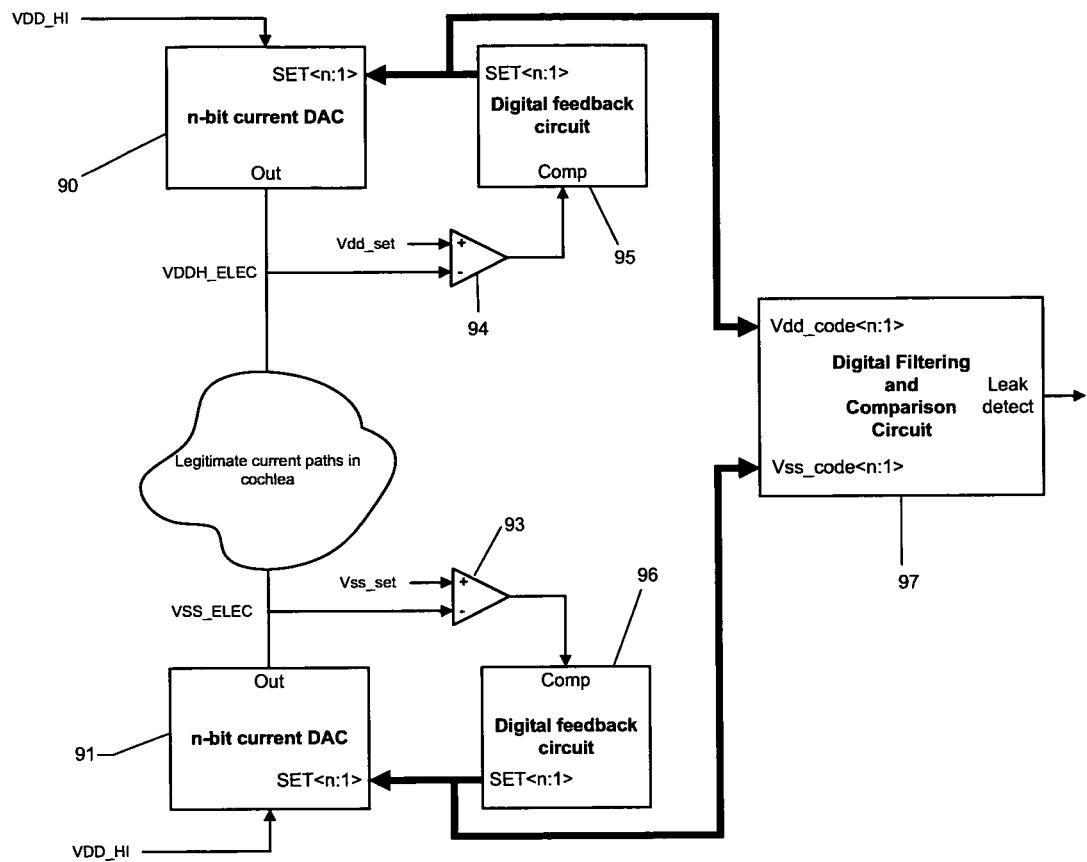
FIG. 3 is a schematic illustration of another implementation.

FIG. 3 illustrates another implementation of the present invention. Instead of using current mirrors to sense the supply and ground currents, the currents get set directly by a current DAC (digital-to-analog converter) 90,91. Digital feedback circuits 95, 96 responsive to respective comparators 93,94 ensure that VDDH_ELEC and VSS_ELEC are maintained at a desired voltage by adjusting the current DAC codes. Thus, at any time, the digital codes for the VDD and VSS current, Vdd_code<n:1> and Vss_code<n:1> represent the actual VDD and VSS currents (since we are setting them directly). A separate digital filtering and comparison circuit compares the VDD and VSS currents that are being set and detects any persistent difference between them, with allowance for differences in timing. A suitable time constant may be, for example, 1 ms or more.

There is a key difference between this and the current mirror approach used in the example shown in FIG. 2. The current mirror approach takes a small (and imperfect) copy of the VDD and VSS currents and compares them. The current DAC approach illustrated in FIG. 3. actually sets the VDD and VSS currents at all times via digitally controlled current DACs. This means that the actual currents going in are known, not just copies. It shifts the filtering and comparison operations into the digital domain. Again, the current DAC approach may use MOSFETs, bipolar transistors etc. as discussed above.

Another way of measuring the current difference is by using the Hall effect. The Hall effect refers to the potential difference (Hall voltage) on opposite sides of a thin sheet of conducting or semiconducting material in the form of a 'Hall bar' (or a van der Pauw element), in this case the power and ground rails VDDH_ELEC and VSS-ELEC through which an electric current is flowing. By measuring the Hall voltage across the element, one can determine the current flowing through the element. A Hall effect device could be used to measure the current difference in an alternative implementation.

Alternatively, the current between VDDH_ELEC and VSS-ELEC could be measured directly. This could then be compared to the expected current. Whilst it is theoretically possible to determine the tissue current, this is very difficult in practice. The benefit of taking the difference between the two rails VDDH_ELEC and VSS-ELEC is that it then does not matter what the current should be and any difference between the currents is due to a fault condition.

Alternatively, the current could be measured at each of the monitors 40, 50 independently before subtraction of the two currents occurs. Any method that can accurately measure the current difference between the power and ground rails VDDH_ELEC and VSS-ELEC can be used.

The implementation described will detect leakage caused by any single failure external to the chip, for example an electrode shorted to some potential, or leakage to the coil. It will also detect many single failures internal to the chip. Some double failures may not be directly detected, but as the first failure to occur will be detected, this is not a significant issue in practice.

A significant advantage of the present invention is that the occurrence of even a fault which had not been anticipated as possible can be detected. Further, it greatly reduces the need for diagnostic and testing processes to run in parallel with the functional operation of the device, thereby enhancing performance by not competing for processor time with the delivery of therapy.

Once a fault condition is detected, the action taken will depend on the nature of the device, and potentially the nature or scale of the current difference. In some cases, it may provide an indication to the user through an existing feedback mechanism that a fault is detected, and that they should contact their clinician to determine how to proceed. In some cases the device may be automatically disabled. In a preferred arrangement, the detection of a fault triggers a software diagnostic process. This can more accurately trace the problem, and depending upon the outcome rectify the fault, indicate to the user that service is required, or shut the device down.

The system 10 has been shown as placed within the implanted portion of a cochlear device. However, the entire circuit or parts of it could be brought outside the chip if desired in a suitable implementation.

Whilst the invention has been described in relation to a cochlear implant, it will be readily appreciated that the invention is equally applicable to other implanted devices. For example, it may be applied to other implanted hearing devices such as implanted hearing aids, middle ear prostheses, brain stem implants and electro-acoustic devices. It may also be used in other implanted medical or other devices. It will further be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of detecting DC current leakage from an electrical circuit of a device implantable in a recipient to tissue of the recipient, the device being configured to conduct current through at least one conductive path having multiple segments including a segment formed by tissue of the recipient, said method including at least the steps of:
    mirroring, for each conductive path, a pre-tissue current and a post-tissue current representing currents at opposite ends of the tissue segment;
    combining the pre-tissue and post-tissue currents to represent a total current;
    determining whether the total current is within a desired tolerance of zero;
    wherein if the total current is not within said desired tolerance of zero, determining that leakage current is present.

2. The method according to claim 1, wherein the mirroring uses current mirroring devices.

3. The method according to claim 2, wherein each current mirroring device uses one of a bipolar current mirror and a MOS current mirror.

4. The method according to claim 1, wherein the implantable device is an implantable hearing device.

5. The method according to claim 4, wherein the implanted device is a cochlear implant and the segments include electrodes of the cochlear implantable.

6. The method according to claim 1, wherein if it is determined that current leakage is present, the method further includes the step of triggering a software diagnostic process.

7. The method according to claim 1, wherein if it is determined that current leakage is present, the method further includes the step of providing an indication of the current leakage.

8. A method of detecting DC current leakage from a device implantable in a recipient to tissue of the recipient, the device being configured to conduct current through at least one conductive path having multiple segments including segments formed by a power rail, a ground rail, and a segment therebetween formed by tissue of the recipient, said method including at least the steps of:
    setting a pre-tissue DAC-code for a first current-output digital-to-analog converter (current DAC) that indirectly represents a current at one end of the tissue segment;
    setting a post-tissue DAC-code for a second current DAC that indirectly represents a current at the other end of the tissue segment;
    using the first current DAC to adjust current at the one end of the tissue segment based on the pre-tissue DAC-code;
    using the second current DAC to adjust current at the other one end of the tissue segment based on the post-tissue DAC-code;
    comparing the pre-tissue DAC-code and the post-tissue DAC-code; and
    if there is an absolute difference greater than a desired tolerance between the pre-tissue code and the post-tissue code, determining that current leakage is present.

9. The method according to claim 8, wherein the implantable device is an implantable hearing device.

10. The method according to claim 9, wherein the implantable device is a cochlear implant.

11. The method according to claim 8, wherein:
    the implantable device includes a power rail and a counterpart ground rail;
    the setting a pre-tissue code includes:
        measuring voltage on the power rail;
        comparing the power rail voltage against a first desired value to produce a first adjustment signal; and
        generating the pre-tissue code based on the first adjustment signal; and
    the setting a post-tissue code includes:
        measuring voltage on the ground rail;
        comparing the ground rail voltage against a second desired value to produce a second adjustment signal; and
        generating the post-tissue code based on the second adjustment signal.

12. The method according to claim 8, wherein if it is determined that current leakage is present, the method further includes at least one of the following steps:
    triggering a software diagnostic process; and
    providing an indication of the current leakage.

13. A device, implantable in a recipient, comprising:
    electrical output driving circuits powered by a respective power and ground rail, each driving circuit being configured to conduct current through a conductive path having multiple segments including segments formed by the power and ground rails, and a segment therebetween formed by tissue of the recipient;

a first current mirror, connected to a proxy node, for tracking a mirrored pre-tissue current, representing a first current passing through the power rail and at least indirectly representing a current at one end of the tissue segment;

a second current mirror, connected to the proxy node, for tracking a mirrored post-tissue current, representing a second current passing through the ground rail and at least indirectly representing a current at the other end of the tissue segment;

a resistor having a first side connected to the proxy node; and a comparator for comparing the voltages on the first side and a second side of the resistor, such that if the comparator detects a difference greater than a desired tolerance, an indication is provided that current leakage is occurring.

14. The implantable device according to claim 13, wherein the implantable device is an implantable hearing device.

15. The implantable device according to claim 14, wherein the implantable device is a cochlear implant.

16. The implantable device according to claim 13, wherein: each current mirror is one of a bipolar current mirror and a MOS current mirror.

17. A device, implantable in a recipient, comprising:

a first DAC-code generator configured to generate a pre-tissue DAC-code that indirectly represents a current at one end of the tissue segment;

a second DAC-code generator configured to generate a post-tissue DAC-code that indirectly represents a current at the other end of the tissue segment;

a first current DAC configured to adjust current at the one end of the tissue segment based on the pre-tissue DAC-code;

a second current DAC configured to adjust current at the other end of the tissue segment based on the post-tissue DAC-code; and a digital comparator for comparing the pre-tissue DAC-code and the post-tissue DAC code, such that if the comparator detects an absolute difference greater than a desired tolerance, an indication is provided that current leakage is occurring.

18. The implantable device according to claim 17, wherein the implantable device is an implantable hearing device.

19. The implantable device according to claim 18, wherein the implantable device is a cochlear implant.

20. The implantable device according to claim 17, further comprising:

a stimulation-power rail; and a counterpart stimulation-ground rail;

a first analog comparator configured to compare the stimulation-power rail voltage against a first desired value and thereby produce a first adjustment signal; and a second analog comparator configured to compare the stimulation-ground rail voltage against a second desired value and thereby produce a second adjustment signal;

wherein the first DAC-code generator is further configured to generate the pre-tissue DAC-code based on the first adjustment signal; and wherein the second DAC-code generator is further configured to generate the post-tissue DAC-code based on the second adjustment signal.

* * * * *

UNITED STATES PATENT AND TRADEMARK OFFICE
CERTIFICATE OF CORRECTION

PATENT NO. : 9,238,140 B2
APPLICATION NO. : 12/438942
DATED : January 19, 2016
INVENTOR(S) : Yashodhan Moghe et al.

It is certified that error appears in the above-identified patent and that said Letters Patent is hereby corrected as shown below:

In the claims,

In Col. 6, line 6, amend "implanted" to --implantable--.

Signed and Sealed this
Fourteenth Day of June, 2016

Michelle K. Lee
*Director of the United States Patent and Trademark Office*